(12) United States Patent
Lukas et al.

(10) Patent No.: US 7,977,043 B2
(45) Date of Patent: Jul. 12, 2011

(54) ASSAYS USEFUL IN DETERMINING CD38 INHIBITION

(75) Inventors: Susan Lukas, Waterbury, CT (US); Gregory Whitten Peet, Sherman, CT (US); Brian Werneburg, Brookfield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 708 days.

(21) Appl. No.: 11/558,479

(22) Filed: Nov. 10, 2006

(65) Prior Publication Data

US 2008/0113871 A1    May 15, 2008

(51) Int. Cl.
    *C12Q 1/00* (2006.01)
(52) U.S. Cl. .................................. 435/4; 435/15; 506/11
(58) Field of Classification Search .................. 435/4
    See application file for complete search history.

(56) References Cited

U.S. PATENT DOCUMENTS

| 6,599,711 B2 | 7/2003 | Crouch et al. | |
| 2003/0064394 A1* | 4/2003 | Ohtake et al. | 435/6 |

OTHER PUBLICATIONS

Perraud et al. Journal of Biological Chemistry. vol. 278(3): 1794-1801; Jan. 17, 2003.*
David L. Clapper et al; "Pyridine Nucleotide Metabolites Stimulate Calcium Release from Sea Urchin Egg Microsomes Desensitized to Inositol Trisphosphate"; The Journal of Biological Chemistry; vol. 262, No. 20, Issue of Jul. 15, pp. 9561-9568, 1987; The American Society of Biological Chemists, Inc., USA.
Deepak A. Deshpande et al; "CD38/cyclic ADP-ribose-mediated Ca2+ signaling contributes to airway smooth muscle hyper-responsiveness"; The FASEB Journal; Mar. 2003; pp. 452-454; vol. 17.
Richard M. Graeff, et al; "High Throughput Fluorescense-Based Assays for Cyclic ADP-Ribose, NAADP, and Their Metabolic Enzymes"; Combinatorial Chemistry and High Throughput Screening; vol. 6;, No. 4; Jun. 2003; pp. 367-379; Bentham Science Publishers.
Richard M. Graeff, et al; "Enzymatic Synthesis and Characterizations of Cyclic GDP-Ribose"; The Journal of Biological Chemistry; vol. 269, No. 48, Issue of Dec. 2, pp. 30260-30267, 1994; The American Society for Biochemistry and Molecular Biology, Inc., USA.
Haruhiro Higashida, et al; "Angiotensin II stimulates cyclic ADP-ribose formation in neonatal rat cardiac myocytes"; Biochem J. (2000), 352, pp. 197-202; 2000 Biochemical Society; Great Britain.
Helene M. Muller-Steffner et al; "Slow-binding Inhibition of NAD+ Glycohydrolase by Arabino Analogues of B-NAD+"; The Journal of Biological Chemistry; vol. 267, No. 14, Issue of May 15, pp. 9606-9611, 1992; The American Society of Biochemistry and Molecular Biology, Inc., USA.
Santiago Partida-Sanchez et al; "Regulation of Dendritic Cell Trafficking by the ADP-Ribosyl Cyclase CD38: Impact on the Development of Humoral Immunity"; Immunity, vol. 20, pp. 279-291, Mar. 2004, Cell Press.
Santiago Partida-Sanchez et al; "Chemotaxis and Calcium Responses of Phagocytes to Formyl Peptide Receptor Ligands Is Differentially Regulated by Cyclic ADP Ribose"; The Journal of Immunology, 2004, 172, pp. 1896-1906; The American Association of Immunologists, Inc., USA.
Anne-Laure Perraud et al; "ADP-ribose gating of the calcium-permeable LTRPC2 channel revealed by Nudix motif homology"; Nature, vol. 411, pp. 595-599; May 31, 2001; Macmillan Magazines Ltd.
Yorikata Sano et al; "Immunocyte Ca2+ Influx System Medicated by LTRPC2"; Science Magazine; Aug. 17, 2001; vol. 293, No. 5533, pp. 1327-1330; Science Magazine.
Katherine A Wall et al; "Inhibition of the intrinsic NAD+ glycohydrolase activity of CD38 by carbocyclic Nad analogues"; Biochem J. (1998) 335, pp. 631-636, Great Britain.
Singh, Pirthipal, Identification of Kinase Inhibitors by an ATP Depletion Method; Assay and Drug Development Technologies, vol. 2, No. 2, 2004 pp. 161-169.

* cited by examiner

*Primary Examiner* — Christopher M Gross
(74) *Attorney, Agent, or Firm* — Michael P. Morris; Edward S. Lazer

(57) ABSTRACT

An assay for use in high-throughput screening of chemical libraries to determine whether compounds in such libraries will inhibit CD38 catalytic activity, and CD38 production of ADPR and cADPR.

8 Claims, 16 Drawing Sheets

CD38 (200 pM)/ADPRase (10 nM)/Myokinase (100 nM)/Luciferase Assay

ADPRase Activity is Inversely Proportional to Luminescent Signal 50 and 100 nM Myokinase Provide Maximum Reduction in Luminescent Signal CD38 (6 nM)/PARP (25 nM) TRF Assay

ASSAYS USEFUL IN DETERMINING CD38 INHIBITION

FIELD OF THE INVENTION

This invention relates to novel high throughput assays useful in determining compounds which will function as inhibitors of the catalysis of nicotinamide adenine dinucleotide hydrolysis to ADP-ribose and nicotinamide adenine dinucleotide cyclization to cyclic ADP-ribose by CD38.

BACKGROUND OF THE INVENTION

CD38 catalyzes the hydrolysis of nicotinamide adenine dinucleotide (NAD$^+$) producing ADP-ribose (ADPR) and also catalyzes cyclization of NAD$^+$ to produce cyclic ADP-ribose (cADPR). Both ADPR and cADPR are physiological messengers required for calcium mobilization and motility of antigen presenting cells involved in the etiology of autoimmunity and inflammation [Perraud et al. (2001) Nature 411: 595-599; Sano et al. (2001) Science 293: 1327-1330; Clapper et al. (1987) J. Biol. Chem. 262: 9561-9568; Partida-Sanchez et al. (2004) J. Immunol. 172: 1896-1906; Partida-Sanchez et al. (2004) Immunity 20:279-291]. CD38/cADPR calcium mobilization has also been shown to have a role in airway hyper-responsiveness (Deshpande et al., (2003) FASEB Journal 17: 452-454. Therefore, potent, specific inhibitors of CD38 appear to be useful in the treatment of autoimmune and inflammatory diseases and diseases associated with hyper-reactivity of the airways, such as asthma. A robust, accurate, high-throughput assay for the identification of CD38 inhibitors would therefore be highly desirable.

Such an assay has not been described previously. Assays for CD38 catalytic activity were either tedious (low throughput) or utilized non-physiological substrates, and involved inefficient detection means that were not amenable to accurate identification of hits from large, diverse compound libraries ($\geqq$10,000 compounds). For example, work published by Wall [Wall et al. (1998) Biochem. J. 335: 631-636] and Higashida [Higashida et al. (2000) Biochem. J. 352: 197-202] utilized radioactively labeled NAD$^+$ substrate, with analysis and measurement of reaction products by scintillation counting, high pressure liquid chromatography (HPLC) and autoradiography. These methods are low-throughput, labor intensive, and environmentally unfriendly.

Muller-Steffner and colleagues published work in 1992 [Muller-Steffner et al. (1992) J. Biol. Chem. 267: 9606-9611], describing data derived from a protocol which utilized a non-physiological NAD$^+$ substrate analog 1,N$^6$-etheno NAD$^+$. CD38 glycohydrolase activity yields the fluorescent product 1,N$^6$-etheno ADP-ribose (excitation $\lambda$=310 nm; emission $\lambda$=410 nm), which has enhanced fluorescence compared to the unhydrolyzed, non-physiological substrate. Graeff and colleagues [Graeff et al. (1994) J. Biol. Chem. 269: 30260-30267] published data derived from a similar protocol in which a second, non-physiological substrate, NAD$^+$ analog, nicotinamide guanine dinucleotide (NGD$^+$), was utilized to assay for CD38 cyclase activity. The product formed in this reaction, cyclic GDP-ribose (cGDPR), was fluorescent and could be monitored with a spectrometer (excitation $\lambda$=300 nm; emission $\lambda$=410 nm). In 2003 Graeff and Lee [Graeff & Lee (2003) Comb. Chem. & High Through. Screen. 6: 367-379] provided details for a third fluorescence based assay constructed to take advantage of CD38 cADPR hydrolytic activity. This assay monitors CD38 dependent hydrolysis of the fluorescent cADPR analog, cyclic inosine diphosphate ribose (cIDPR). As cIDPR is hydrolyzed by CD38, loss of fluorescent signal is monitored with a spectrometer (excitation $\lambda$=310 nm; emission $\lambda$=410 nm). In the aforementioned assays, the detection wavelength was below 450 nm, a range in which many compounds in today's modern, diverse libraries absorb light, thus leading to spectral interference and erroneous results (false positive data).

SUMMARY OF THE INVENTION

The present invention describes the first assays for efficient and accurate identification of inhibitors of CD38 production of ADPR and cADPR, useful in the treatment of autoimmune and inflammatory diseases, and diseases associated with airway hyper-responsiveness. The invention has specific utility in identifying physiologically relevant CD38 inhibitors from large, diverse compound libraries, which libraries comprise compounds that interfere with light based (<500 nm) detection assays. Selective CD38 inhibitors are identified by high-throughput assays that generate luminescent and time resolved fluorescent ($\lambda$=620 nm) signals for detection.

Eu-labeled streptavidin (PerkinElmer: catalog #1244-360; 100 μg/mL) was diluted 1:50 in PerkinElmer DELFIA® Assay Buffer (PerkinElmer: catalog #1244-111), and a 100 μL aliquot of this solution, containing 0.2 μg Eu-labeled streptavidin, was added to each well of the plate. After a sixty minute incubation at 25° C., the plate was washed 6 times with 50 mM Tris-HCl pH 7.4, 150 mM NaCl, 0.05% Tween-20 and 0.2% bovine serum albumin.

A 200 μL aliquot of PerkinElmer DELFIA® Enhancement Solution (PerkinElmer: catalog #4001-0010) was added to each well, prior to sealing the wells with an adhesive cover and shaking the plate for 30 min. Upon removal of the adhesive cover, the time resolved fluorescence signal was measured at exλ=360 nm and emλ=620 nm with an LJL plate reader (LJL Biosystems Analyst AD) using Molecular Devices software (Molecular Devices—CriterionHost v2.01.00). Percent of control time resolved fluorescence signal, where 100% of control is the change in time resolved fluorescence signal in the presence of CD38 and absence of compound, was plotted vs. [compound]. The data were fit to the Hill equation with Sigma Plot 9 to obtain $IC_{50}$s.

Figure 10:
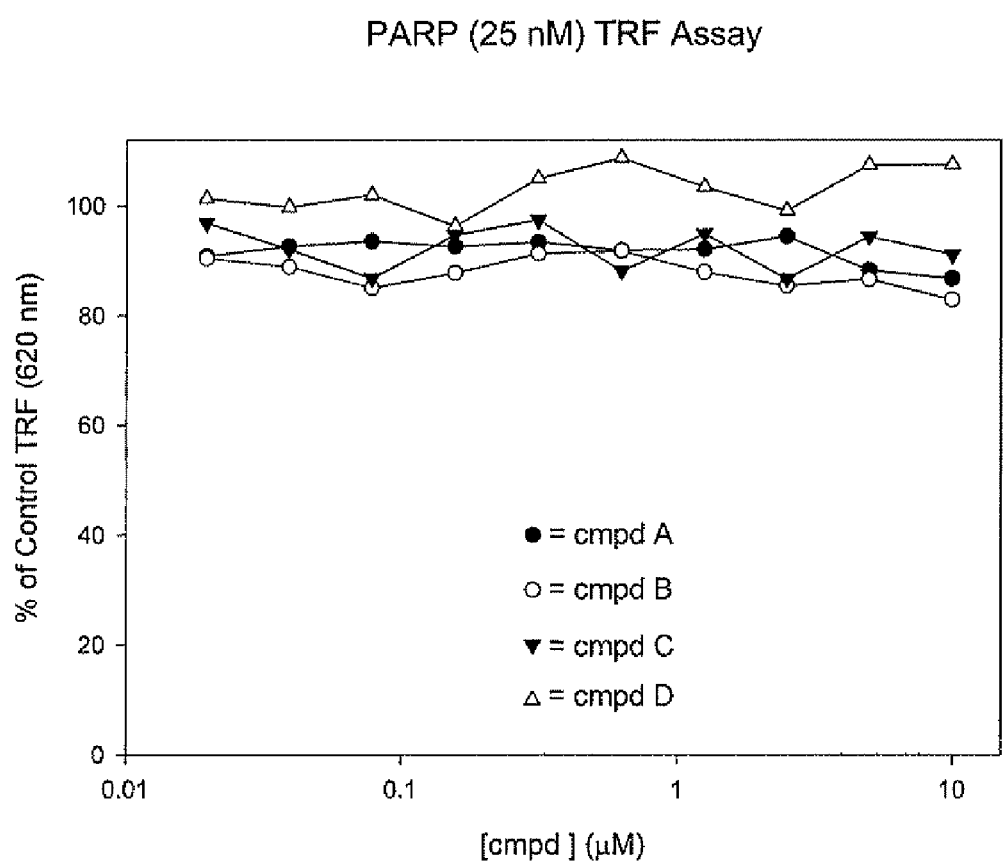

FIG. 10 is graph showing that compounds A, B, C and D are not inhibitors of PARP, and therefore are specific inhibitors of CD38. Compound inhibition (n=2) assays were performed in histone (Trevigen: catalog #4667-50-07) coated 96 well plates (Greiner: catalog #655074). A 40 μL solution, containing 50 mM Tris-HCl (pH 8.0), 25 mM $MgCl_2$, 0.05% CHAPS, 1% DMSO, compound A, B, C or D at various concentrations, 4.17 μM 6-Biotin-17-$NAD^+$, 20.9 μM $NAD^+$ and 0.0125 μg/μL sheared DNA, was preincubated at 37° C. for 15 min. A 10 μL aliquot of 125 nM PARP-1 and 250 mM DTT in assay buffer (50 mM Tris-HCl (pH 8.0), 25 mM $MgCl_2$, 0.05% CHAPS) was then added to initiate catalysis of histone ADP-ribosylation and biotinyl-ADP-ribosylation with a final concentration of 25 nM PARP-1. Upon incubation of the 50 μL reaction for 60 min at 37° C., the plate was washed 3 times with 50 mM Tris-HCl pH 7.4, 150 mM NaCl, 0.05% Tween-20 and 0.2% bovine serum albumin.

Eu-labeled streptavidin (PerkinElmer: catalog #1244-360; 100 μg/mL) was diluted 1:50 (v:v) in PerkinElmer DELFIA® Assay Buffer (PerkinElmer: catalog #1244-111), and a 100 μL aliquot of this solution, containing 0.2 μg Eu-labeled streptavidin, was added to each well of the plate. After 60 min incubation at 25° C., the plate was washed 6 times with 50 mM Tris-HCl pH 7.4, 150 mM NaCl, 0.05% Tween-20 and 0.2% bovine serum albumin.

A 200 μL aliquot of PerkinElmer DELFIA® Enhancement Solution (PerkinElmer: catalog #4001-0010) was added to each well, prior to sealing the wells with an adhesive cover and shaking the plate for 30 minutes. Upon removal of the adhesive cover, the time resolved fluorescence signal was measured at exλ=360 nm and emλ=620 nm with an LJL plate reader (LJL Biosystems Analyst AD) using Molecular Devices software (Molecular Devices—CriterionHost v2.01.00). Percent of control time resolved fluorescence signal for inhibitor samples, based on the average PARP-1 control (no compound) time resolved fluorescence, was plotted vs. [compound]. The data were fit to the Hill equation with Sigma Plot 9 to obtain $IC_{50}$s.

DETAILED DESCRIPTION OF THE INVENTION

The present invention describes the first accurate high-throughput assays for CD38 dependent catalysis of $NAD^+$ hydrolysis, producing ADP-ribose (ADPR), and for CD38 dependent catalysis of NAD+ cyclization to produce cyclic ADP-ribose (cADPR). The detection means are efficient and accurate for identifying physiologically relevant CD38 dependent inhibitors from large, diverse compound libraries, containing compounds that interfere with light based detection means below 500 nm.

The first assay for detection of CD38 dependent ADPR production and inhibitor identification involves two coupling enzymes, ADP-ribose pyrophosphatase (ADPRase) and myokinase (adenylate kinase), that link the catalytic formation of one equivalent of ADPR by CD38 (Step 1) to the catalytic consumption of one equivalent of ATP in Steps 2 and 3 as illustrated in Scheme 1.

Scheme 1

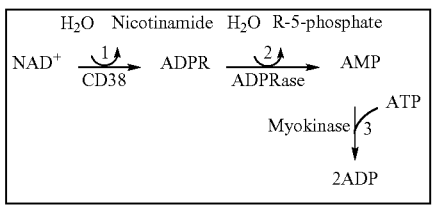

Residual ATP is then consumed in Step 4 by luciferase-catalyzed oxidation of luciferin [(S)-2-(6-hydroxy-2-benzothiazolyl)-2-thiazoline-4-carboxylic acid; 4,5-dihydro-2-(6-hydroxy-2-benzothiazolyl)-4-thiazolecarboxylic acid], to generate a luminescent signal (hv), as illustrated in Scheme 2.

Scheme 2

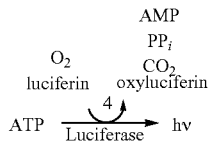

The greater the CD38, ADPRase and myokinase activity generated in Steps 1-3, the less luminescent signal generated in Step 4; the less CD38, ADPRase and myokinase activity generated in Steps 1-3, the greater the luminescent signal (hv) generated at in Step 4. Thus, inhibitors of CD38 manifest an increase in luminescent signal.

Inhibitors of ADPRase and myokinase also result in an increased luminescent signal. Inhibitors of ADPRase and/or myokinase are distinguished from specific CD38 inhibitors by removing Step 1 in a follow-up assay initiated with ADPRase substrate, ADPR. Specific inhibitors of CD38 do not produce an increased luminescent signal in this follow-up assay.

Figure 1:
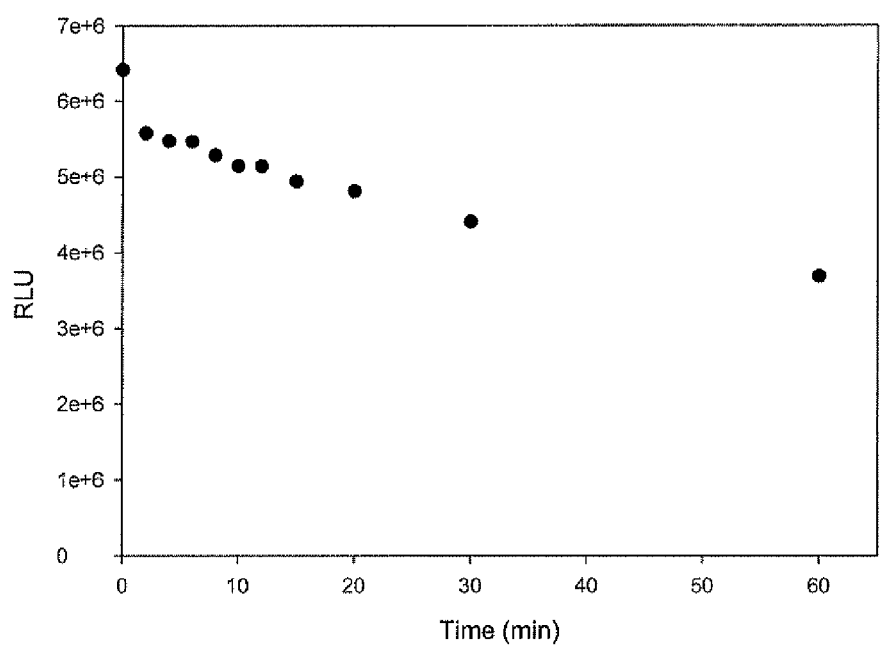
FIG. 1 is a graph showing the consumption of ATP, corresponding to catalysis of ADPR production by CD38 as measured by a decrease in relative luminescence units (RLU) over time in the CD38/ADPRase/myokinase/luciferase assay.

Steps 1-3 (Scheme 1) are performed in a homogeneous reaction (15-40 μL; 25° C.), containing 50 mM HEPES at pH 7.5, 100 mM KCl, 5 mM MgCl$_2$, 1 mM DTT or 200 μM TCEP, 0.05% to 0.1% CHAPS, 4 μM ATP, preferably at least 12.5 μM and more preferably 25 μM NAD+, preferably at least 111 pM and more preferably 200 pM human CD38 ectoenzyme domain 45-299 with a YV amino-terminal fusion and N100D, N164A, N209D and N219D mutations (6 H amino-terminal fusion of CD38 ectoenzyme domain 45-299 with N100D, N164A, N209D and N219D mutations, and wild type CD38 proteins from multiple species and any other catalytically active CD38 derived proteins may be used), preferably at least 1.25 nM and more preferably 10 nM NUDT9 ADPRase and preferably at least 50 nM and more preferably 100 nM myokinase. Up to 5% DMSO may be added to solubilize compounds. Steps 1-3 have an incubation time of preferably 20 to 60 minutes, prior to the addition of 40 μL of PKLight reaction mixture in Step 4, resulting in ATP consumption of 20 to 50%. PKLight protein kinase reagent from Cambrex (U.S. Pat. No. 6,599,711) contains the luciferase and luciferin required for luminescence production in Step 4. An incubation time of 5-15 min for Step 4 is preferred for consuming residual ATP from Steps 1-3 to generate luminescence for the detection of CD38 dependent ADPR production. Relative luminescence units (RLU) are read with a luminescence detection plate reader to monitor the consumption of ATP that is directly proportional to the catalysis of ADPR production by CD38 in Steps 1-3, where one equivalent of ATP is consumed for every equivalent of ADPR produced (FIG. 1).

Figure 2:
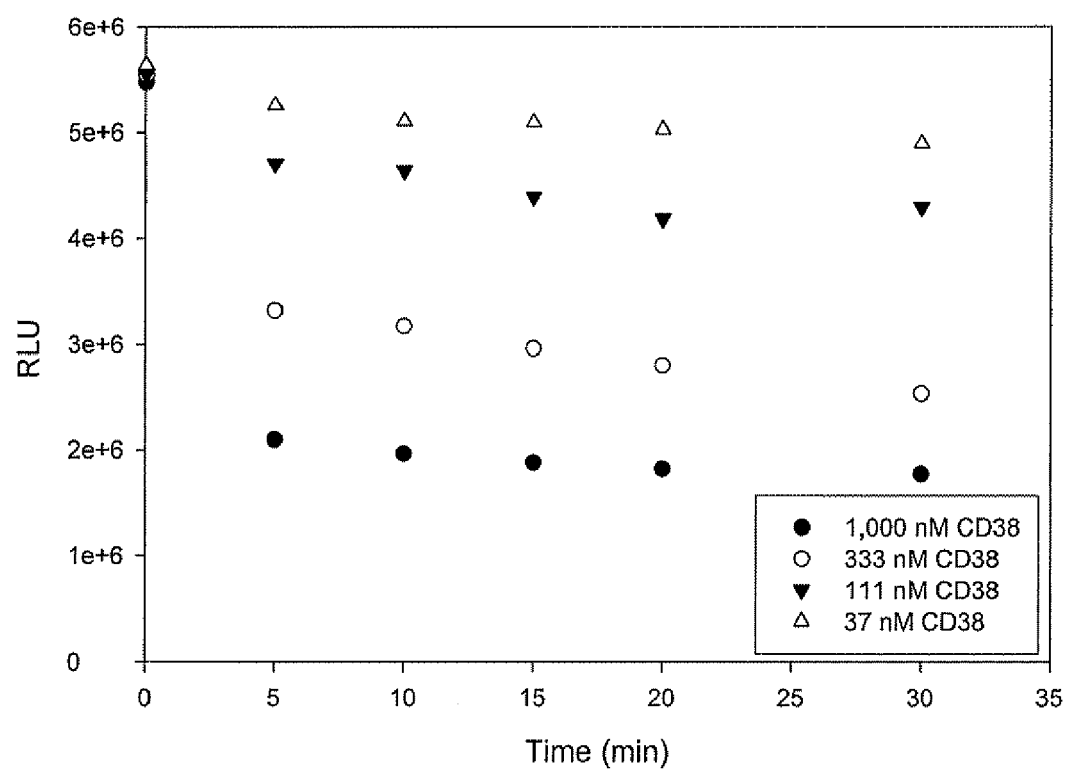
FIG. 2 is a graph showing increasing concentrations of CD38 result in increased consumption of ATP and a decrease in the luminescent signal in the CD38/ADPRase/myokinase/luciferase assay.

The greater the CD38, ADPRase and myokinase activity generated in Steps 1-3, the greater the consumption of ATP, and the lower the luminescent signal generated in Step 4 from residual ATP. This is exhibited in FIG. 2, where an increase in CD38 concentration leads to a decrease in luminescence.

Figure 3A:
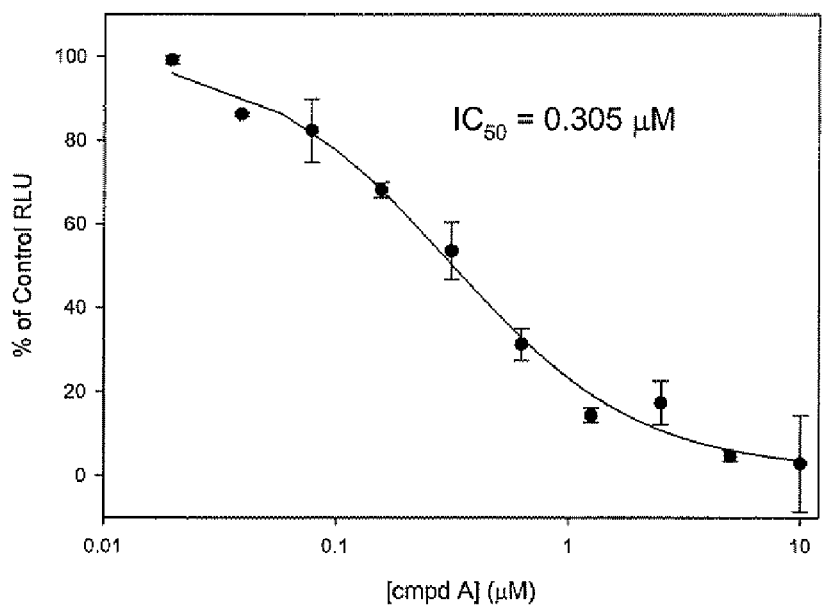
FIGS. 3A, 3B, 3C and 3D include IC$_{50}$ curves showing inhibition of CD38 by four inhibitor compounds A, B, C and D (respectively) in the CD38/ADPRase/myokinase/luciferase assay. Compound inhibition assays (n=2) were performed in Lumitrac 200 medium binding white 96-well plates (E & K Scientific: catalog #EK-25075). CD38 ectoenzyme domain 45-299 (533 pM) with a YV amino-terminal fusion and four mutations, N100D, N164A, N209D and N219D, was preincubated for 1 hr at 25° C. with compounds at various concentrations in a 15 µL solution, containing Buffer A: 50 mM HEPES (pH 7.5), 100 mM KCl, 5 mM MgCl$_2$, 200 µM TCEP (Pierce: catalog #77720), 0.05% CHAPS, 0.2% bovine serum albumin and 2.66% DMSO. Following the preincubation, a 20 µL solution, containing Buffer A, 20 nM GST-ADPRase (NUDT9), 200 nM myokinase (Sigma: catalog #M-5520) and 8 µM ATP (Amersham Pharmacia: catalog #272056), was added. To initiate catalysis, a 5 µL aliquot of 200 µM NAD$^+$ (Sigma catalog #N-1511) in Buffer A was added to the 35 µL solution, yielding a 40 µL reaction mixture, containing 200 pM CD38, 10 nM GST-ADPRase (NUDT9), 100 nM myokinase, 4 µM ATP, 25 µM NAD$^+$, compound A, B, C or D at various concentrations, and 1% DMSO in Buffer A. The reaction was allowed to proceed for 40 min at 25° C. An aliquot of 40 µL of neat PKLight solution (Cambrex catalog #LT07-500) was then added to the reaction mixture and the plate was read within 5-10 min on an LJL plate reader (LJL Biosystems Analyst AD) in the luminescence mode using Molecular Devices software (Molecular Devices—CriterionHost v2.01.00). Percent of control relative luciferase units (RLU), where 100% of control is the change in RLU in the presence of CD38 and absence of compound, is plotted vs. [compound]. The data were fit to the Hill equation with Sigma Plot 9 to obtain IC$_{50}$s.
Figure 3B:
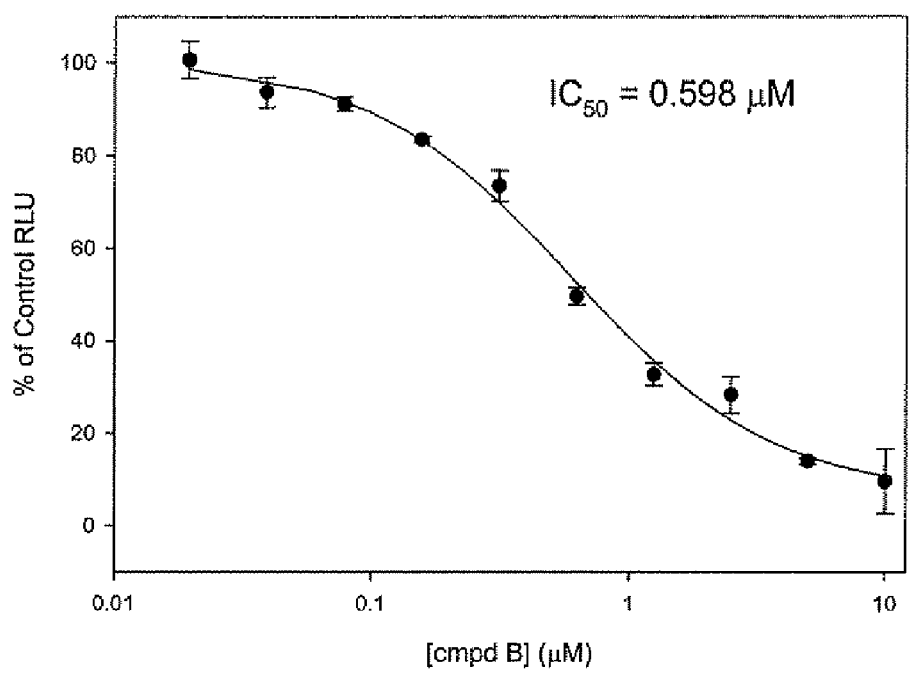
Figure 3C:
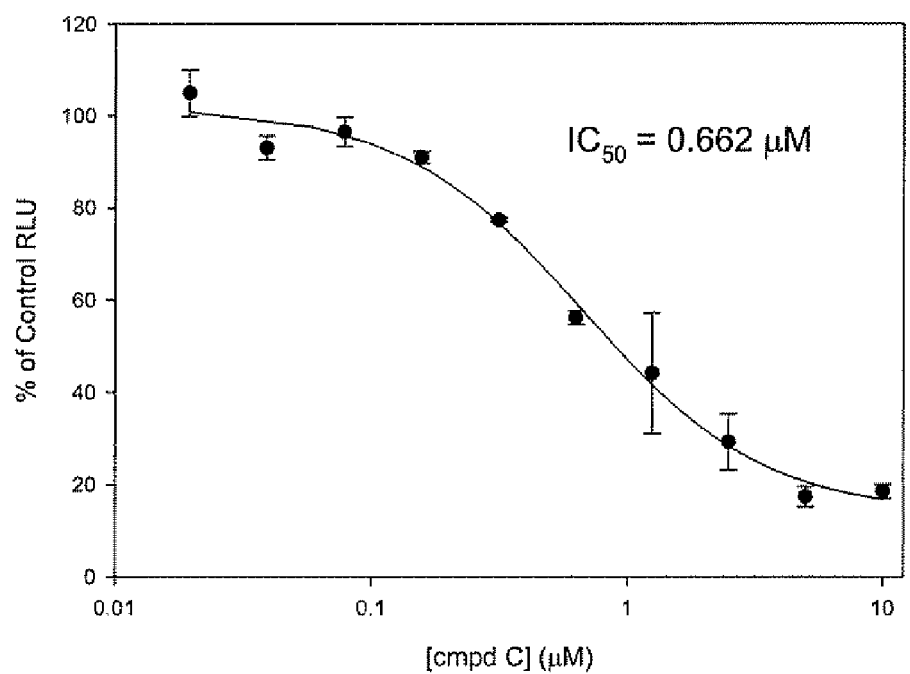
Figure 3D:
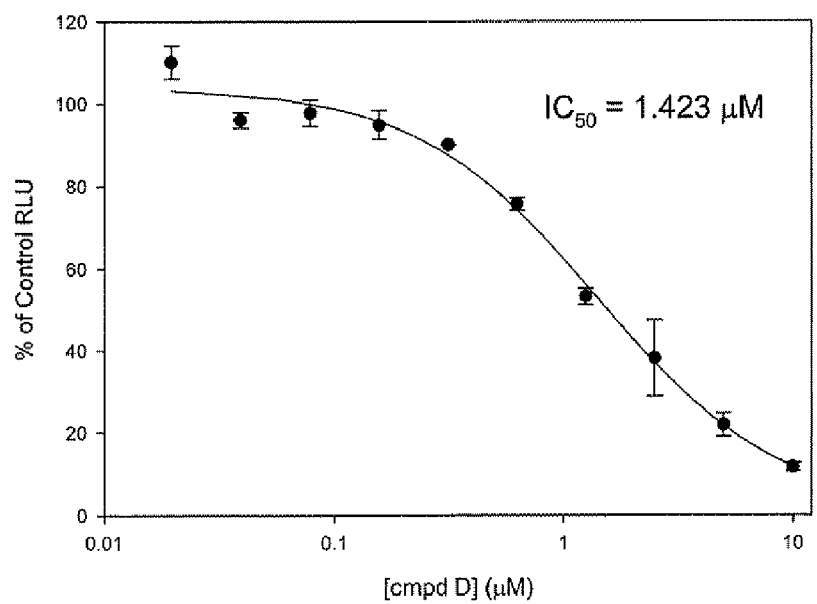

The relative luminescence units produced are inversely proportional to CD38 activity; thus, inhibition of CD38 manifests an increase in relative luminescence units. The assay is ideal for identifying CD38 inhibitors in high-throughput (≧96 well format) from large compound libraries. The concentration of inhibitor required for 50% inhibition of 200 pM CD38 is determined by monitoring the increase in luminescence signal with increasing inhibitor concentration, as shown in FIG. 3A for compound A.

Inhibitors of ADPRase and myokinase would also result in increased luminescent signal. Therefore, a follow-up assay is required to distinguish specific inhibitors of CD38 from inhibitors of ADPRase and myokinase, as well as non-specific inhibitors of CD38 that cross react with either ADPRase or myokinase. The follow-up counter screen for identifying ADPRase and myokinase inhibitors entails removing Step 1 of Scheme 1 in an assay that is initiated with ADPRase substrate, ADPR. Specific inhibitors of CD38 do not produce an increased luminescent signal in the follow-up ADPRase/myokinase/luciferase assay. Steps 2-3 (Scheme 1) are performed in a homogeneous reaction (15-40 μL), containing 50 mM HEPES at pH 7.5, 100 mM KCl, 5 mM MgCl$_2$, 1 mM DTT or 200 μM TCEP, 0.05% CHAPS, 4 μM ATP, 50 μM ADPR, 0.3-5 nM NUDT9 ADPRase, 100 nM myokinase. Up to 5% DMSO may be added to solubilize compounds in this assay format.

Steps 2-3 have an incubation time of preferably 10 to 40 minutes, prior to the addition of 40 μL of PKLight reaction mixture in Step 4, resulting in ATP consumption of 20 to 50%. PKLight protein kinase reagent from Cambrex (U.S. Pat. No. 6,599,711) contains the luciferase and luciferin required for luminescence production in Step 4 (Scheme 2).

Figure 4:
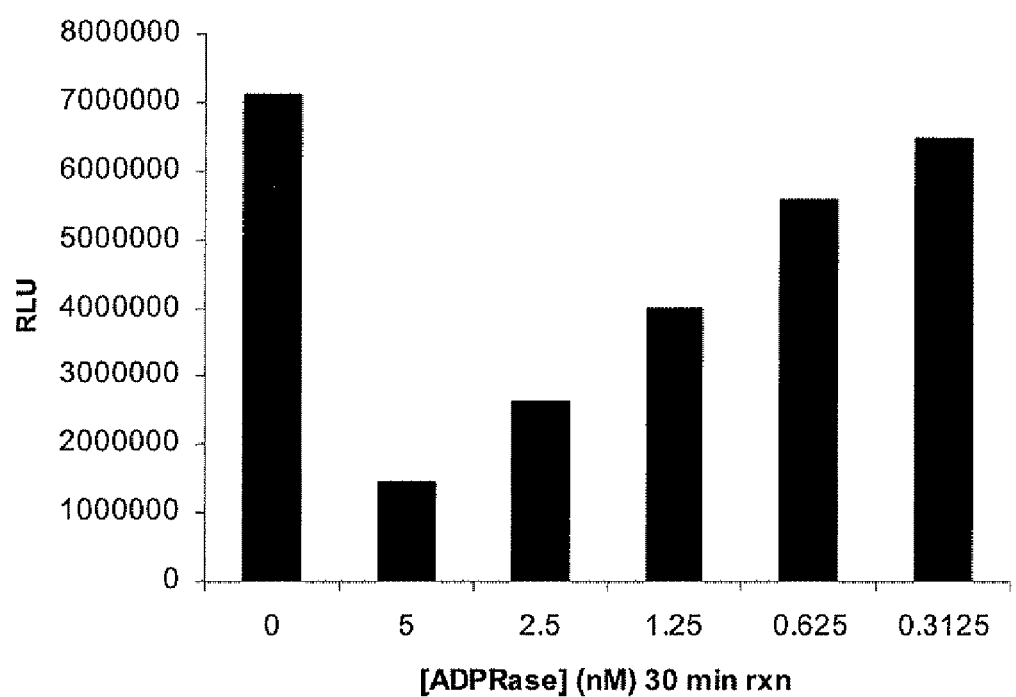
FIG. 4 is a graph showing increasing concentrations of ADPRase result in increased consumption of ATP and a decrease in the luminescent signal in the ADPRase/myokinase/luciferase assay.
Figure 5:
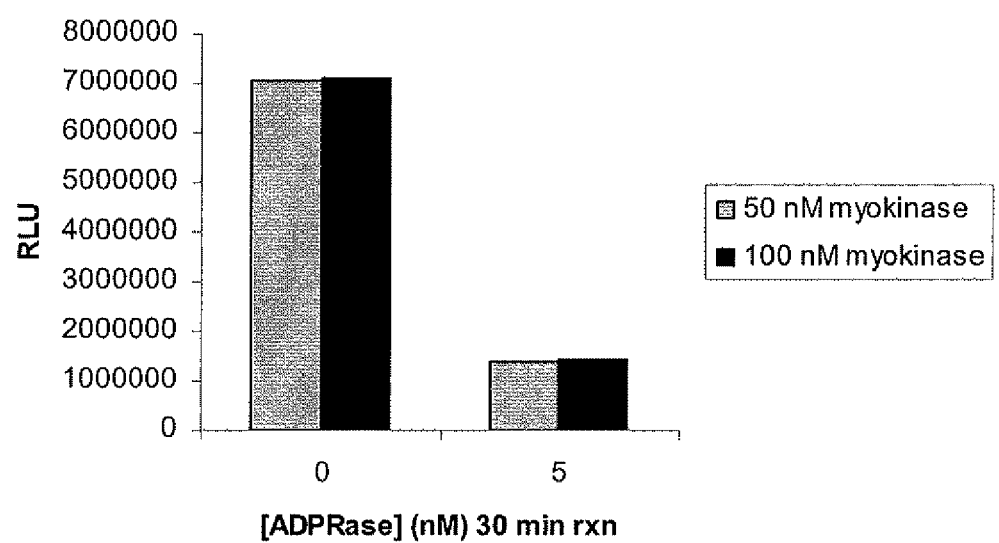
FIG. 5 is a graph showing that 50 nM and 100 nM of myokinase are equally effective in reducing the luminescent signal in the ADPRase/myokinase/luciferase assay by consuming the residual ATP that is left to generate luminescence in the presence of 0 nM ADPRase (minimum AMP levels, maximum ATP levels) or 5 nM ADPRase (higher AMP levels, lower ATP levels).

An incubation time of 5-15 min for Step 4 is preferred for consuming residual ATP from Steps 2-3 to generate luminescence (hv): ADPRase activity is inversely proportional to the luminescent signal produced in Step 4, as shown in FIG. 4, in the ADPRase/myokinase counterscreen. Myokinase activity is also inversely proportional to the luminescent signal produced in Step 4. As shown in FIG. 5, both 50 and 100 nM myokinase are observed to provide a maximum reduction in luminescent signal.

Figure 6:
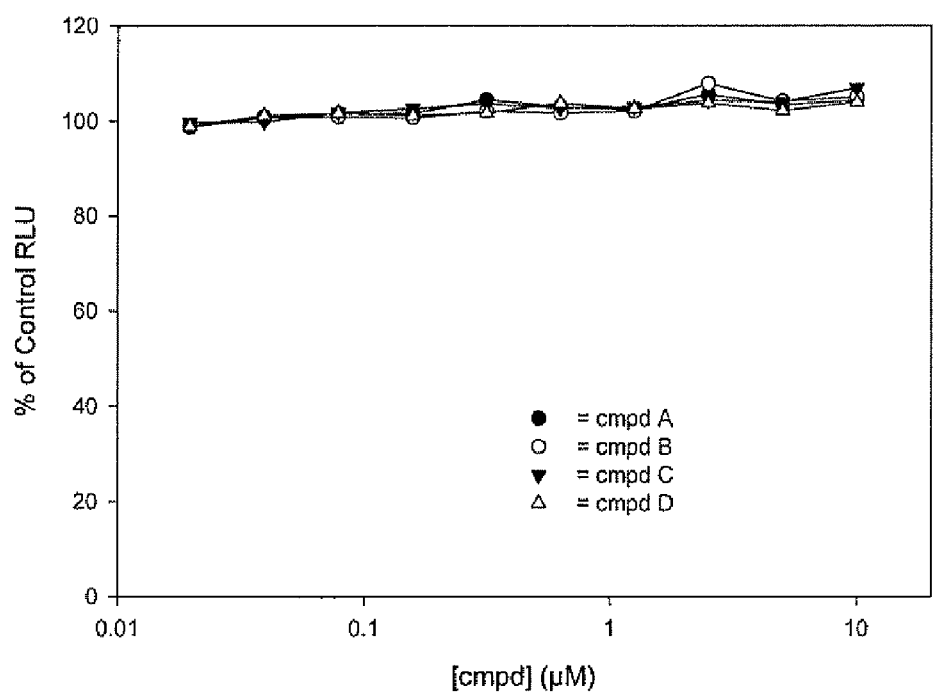
FIG. 6 is a graph showing that compounds A, B, C and D are not inhibitors of ADPRase or myokinase activity and therefore are specific inhibitors of CD38. Compound inhibition assays (n=2) were performed in Lumitrac 200 medium binding white 96-well plates (E & K Scientific: catalog #EK-25075). GST-ADPRase (NUDT9) (13.3 nM) was preincubated for 1 hr at 25° C. with compounds at various concentrations in a 15 μL solution containing Buffer A: 50 mM HEPES (pH 7.5), 100 mM KCl, 5 mM $MgCl_2$, 200 μM TCEP, 0.05% CHAPS, 0.2% bovine serum albumin and 2.66% DMSO. Following the preincubation, a 20 μL solution, containing Buffer A, 200 nM myokinase (Sigma: catalog #M-5520) and 8 μM ATP (Amersham Pharmacia: catalog #272056), was added. To initiate catalysis, a 5 μL aliquot of 400 μM ADPR (Sigma catalog #A-0752) in Buffer A was added to the 35 μL solution, yielding a 40 μL reaction mixture containing 5 nM GST-ADPRase (NUDT9), 100 nM myokinase, 4 μM ATP, 50 μM ADPR, compound A, B, C or D at various concentrations and 1% DMSO in Buffer A. The reaction was allowed to proceed for 30 min at 25° C. An aliquot of 40 μL neat PKLight solution (Cambrex catalog #LT07-500) was then added to the reaction mixture and the plate was read within 5-10 min on an LJL plate reader (LJL Biosystems Analyst AD) in the luminescence mode using Molecular Devices software (Molecular Devices—CriterionHost v2.01.00). Percent of control relative luciferase units (RLU), where 100% of control is the change in RLU in the presence of ADPRase and absence of compound, is plotted vs. [compound]. The data were fit to the Hill equation with Sigma Plot 9 to obtain $IC_{50}$s.

Inhibitors of ADPRase and myokinase can be readily detected by an increase in luminescence in this follow-up counter screen, involving Steps 2-4. Thus, specific inhibitors of CD38, such as compounds A, B, C and D, are characterized by the absence of inhibition in the ADPRase/myokinase/luciferase assay (FIG. 6). Compounds A, B, C and D are identified as specific inhibitors of CD38, by inhibition observed in FIGS. 3A, 3B, 3C and 3D, and the absence of inhibition in the counter screen.

Specific inhibitors of CD38 identified by the above assays may be confirmed and further characterized by a second assay of CD38 catalysis of NAD$^+$ hydrolysis and cyclization. The second assay for detection of CD38 dependent ADPR and cADPR production is by competition between CD38 and poly ADP-ribosyl polymerase (PARP) for their physiological substrate, NAD$^+$, and analogue, B-NAD$^+$ (6-biotin-17-nicotinamide adenine dinucleotide from Trevigen #4670-500-01) as illustrated in Scheme 3. PARP-1 or other PARP isoforms, such as PARP-3, may be used in this assay.

Scheme 3

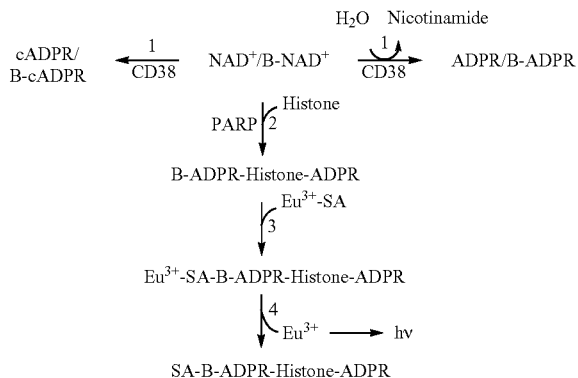

B-NAD$^+$ and NAD$^+$ are both substrates of the CD38 and PARP enzymes. CD38 dependent production of ADPR/B-ADPR and cADPR/B-cADPR in Step 1 is assayed indirectly by depletion of the PARP substrates, NAD$^+$ and B-NAD$^+$. Both NAD$^+$ and B-NAD$^+$ are substrates for CD38 in Step 1, where a mixture of NAD$^+$/B-NAD$^+$ in a ratio of preferably 1:1 to 15:1 and more preferably at 5:1 with a final concentration of NAD$^+$ of preferably at least 12.5 μM and more preferably 20-25 μM, is utilized in a 40 μL reaction (15 min at 37° C.), containing 50 mM Tris-HCl at pH 8.0, 25 mM MgCl$_2$, 0.05% CHAPS, 0.5 μg sheared or sonicated DNA (required to activate PARP in Step 2), and 5-7 nM human CD38 ectoenzyme domain 45-299 with a YV amino-terminal fusion and N100D, N164A, N209D and N219D mutations. Inhibitor compounds may be solubilized with up to 5% DMSO. Incubation time for CD38 is preferably between 15 minutes and 2 hours. Preferably, at least 75% of the NAD$^+$/B-NAD$^+$ substrate is consumed by CD38 prior to Step 2.

In Step 2, PARP-1 utilizes residual NAD$^+$/B-NAD$^+$ from Step 1 in catalyzing ADP-ribosylation and B-ADP-ribosylation of immobilized histone proteins. CD38 activity is quenched by the addition of 50 mM of a suitable reducing agent such as dithiothreitol (DTT), dithioerythritol (DTE) or beta-mercaptoethanol. A histone protein, such as HI, HII-A, HIII-S or HVIII-S, preferably HI, (0.09375 μg/well) is immobilized in 96 well protein binding plates by plating in phosphate buffered saline at pH 7.0-7.2. The histone plates are blocked with 2% bovine serum albumin and washed with 50 mM Tris-HCl at pH 7.4, 150 mM NaCl, 0.05% Tween-20 and 0.2% BSA prior to the addition of the 40 μL Step 1 reaction.

Step 2 is initiated with the addition of 10 μL of PARP-1 (25-110 nM final concentration: sufficient for converting all residual NAD$^+$ into product within 60 min) and DTT (50 mM final concentration). Step 2 proceeds for preferably 60 minutes at preferably 37° C., followed by washing with 50 mM Tris-HCl at pH 7.4, 150 mM NaCl, 0.05% Tween-20 and 0.2% BSA.

Figure 7:
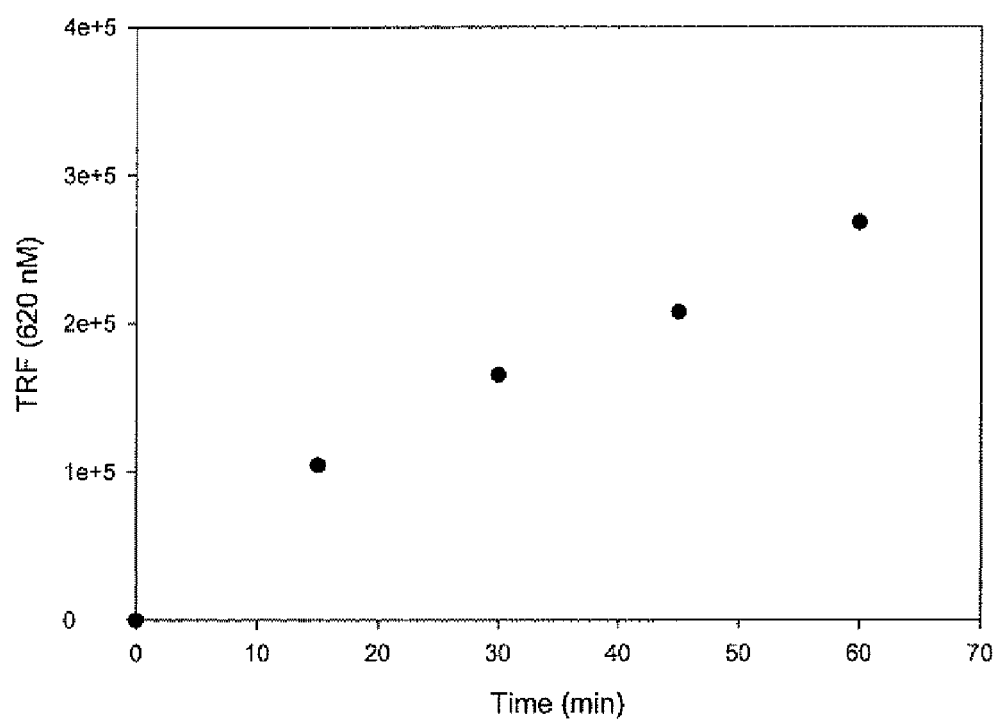
FIG. 7 is a graph showing an increase in time resolved fluorescence (TRF) over time as a result of PARP-1 activity in the PARP TRF assay.

Steps 3 and 4 involve the binding of Eu$^{3+}$-SA (Eu$^{3+}$ chelated streptavidin from Perkin Elmer #1244-360) to B-ADPR on immobilized histone, washing away unbound Eu$^{3+}$-SA, and releasing Eu$^{3+}$ for enhanced time resolved fluorescence. Thus, Eu$^{3+}$ chelated streptavidin (Eu$^{3+}$-SA) is added (200 ng) to the histone coated plates in Step 3, followed by preferably a 60 min incubation at 25° C. to allow for binding of Eu$^{3+}$-SA to B-ADPR that was covalently linked to immobilized histone in Step 2. Unbound Eu$^{3+}$-SA is removed by washing with 50 mM Tris-HCl at pH 7.4, 150 mM NaCl, 0.05% Tween-20 and 0.2% BSA, before the addition of DELFIA® enhancement solution (Perkin Elmer #4001-0010) in Step 4 to release Eu$^{3+}$ for enhanced time resolved fluorescence (hv: excitation λ=360 nm; emission λ=620 nm) detection in a fluorescent plate reader. The preferred incubation period for enhancement of time resolved fluorescence signal in Step 4 is 30 minutes with shaking and 170 minutes without shaking. Steps 2-4 are described in a Perkin Elmer Life Sciences application note [Perkin Elmer (2002) Appl. Note 1234-9865-01]. The Eu$^{3+}$ time resolved fluorescence signal generated from PARP-1 catalysis is directly proportional to PARP-1 activity, as shown in FIG. 7, where a time dependent increase in time resolved fluorescence signal is observed. Other lanthanide ion chelates may be used in addition to the Europium (Eu) chelate mentioned above; for example, Samarium (Sm), Terbium (Tb) or Dysprosium (Dy) ions emit fluorescence when bound to specific ligands.

Figure 8:
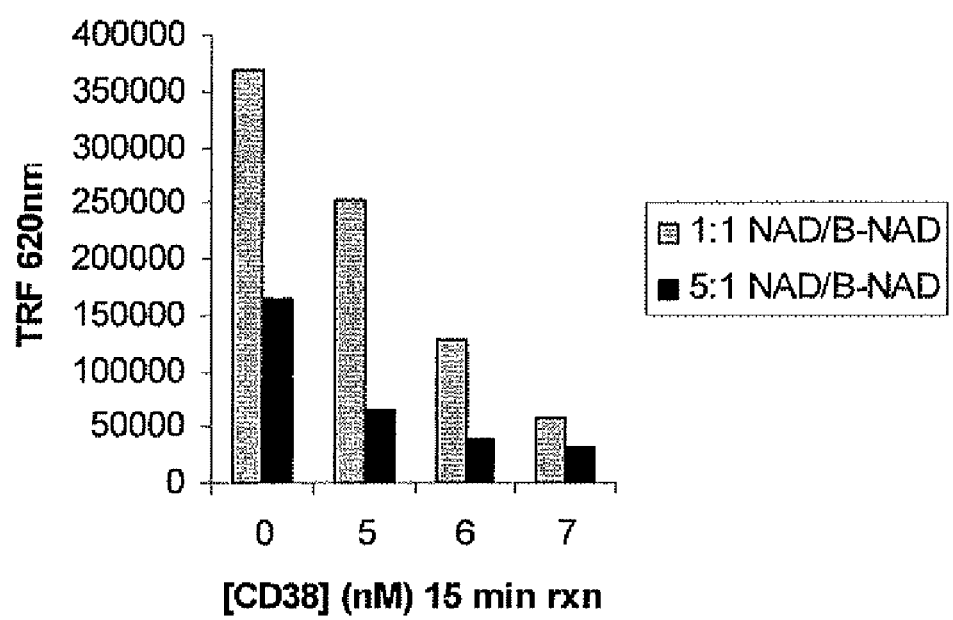
FIG. 8 is a graph showing increased concentrations of CD38 result in a decrease in TRF in the CD38/PARP TRF due to consumption of $NAD^+$/B-$NAD^+$.
Figure 9A:
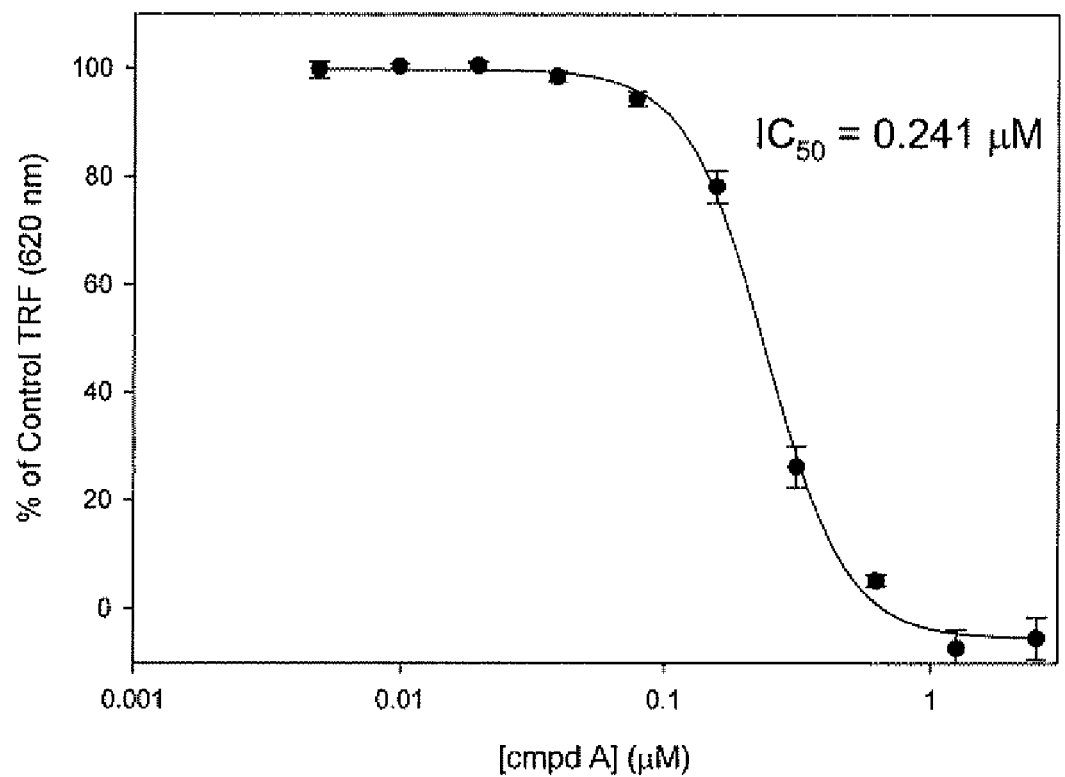
FIGS. 9A, 9B, 9C and 9D include $IC_{50}$ curves, showing inhibition of CD38 by four inhibitor compounds A, B, C and D (respectively) in the CD38/PARP TRF assay. Compound inhibition assays were performed (n=2) in histone (Trevigen: catalog #4667-50-07) coated 96 well plates (Greiner: catalog #655074). Human CD38 ectoenzyme domain 45-299 (8 nM) with a YV amino-terminal fusion and four mutations, N100D, N164A, N209D and N219D, was preincubated for 1 hr at 25° C. with compounds at various concentrations in a 30 μL solution, containing 50 mM Tris-HCl (pH 8.0), 25 mM $MgCl_2$, 0.05% CHAPS and 1.33% DMSO. To initiate catalysis, a 10 μL aliquot, containing 50 mM Tris-HCl (pH 8.0), 25 mM $MgCl_2$, 0.05% CHAPS, 16.67 μM 6-Biotin-17-$NAD^+$ (Trevigen: catalog #4670-500-01), 83.7 μM $NAD^+$ and 0.05 μg/μL sheared DNA, was added to the 30 μL solution. The 40 μL reaction mixture, containing 50 mM Tris-HCl (pH 8.0), 25 mM $MgCl_2$, 0.05% CHAPS, 1% DMSO, 6 nM CD38, compound A, B, C or D at various concentrations, 4.17 μM 6-Biotin-17-$NAD^+$, 20.9 μM $NAD^+$ and 0.0125 μg/μL sheared DNA, was incubated at 37° C. for 15 min. A 10 μL aliquot of 125 nM PARP-1 and 250 mM DTT in assay buffer (50 mM Tris-HCl (pH 8.0), 25 mM $MgCl_2$, 0.05% CHAPS) was then added to inactivate CD38 with a final concentration of 50 mM DTT and initiate catalysis of histone ADP-ribosylation and biotinyl-ADP-ribosylation with a final concentration of 25 nM PARP-1. Upon incubation of the 50 μL reaction for 60 minutes at 37° C., the plate was washed 3 times with 50 mM Tris-HCl pH 7.4, 150 mM NaCl, 0.05% Tween-20 and 0.2% bovine serum albumin.
Figure 9B:
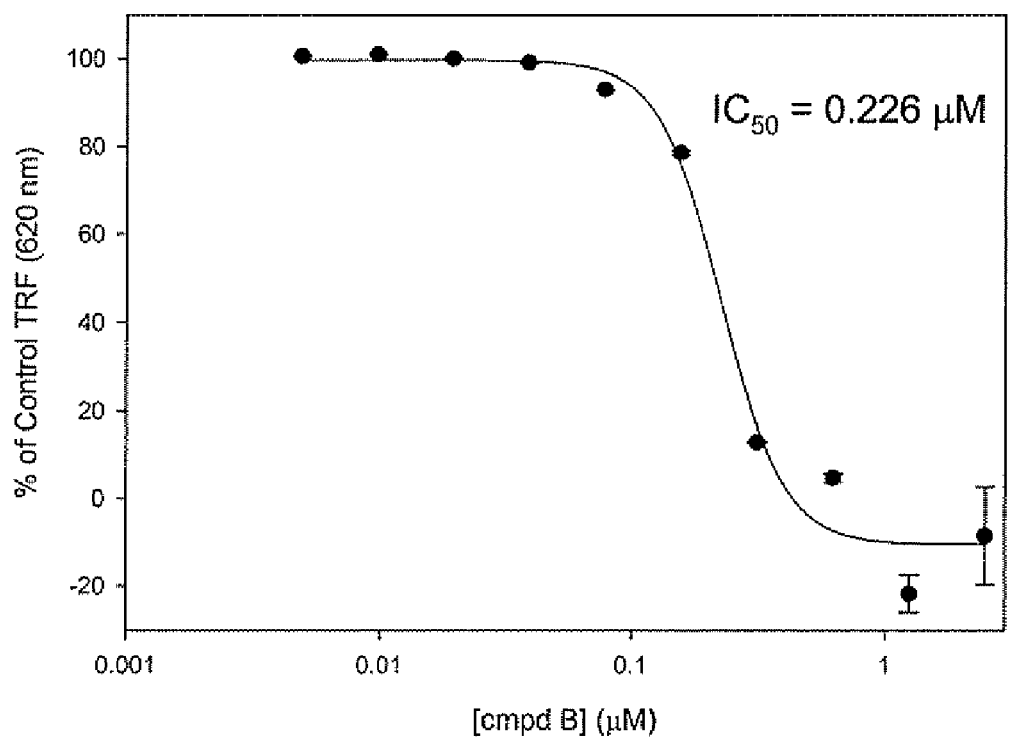
Figure 9C:
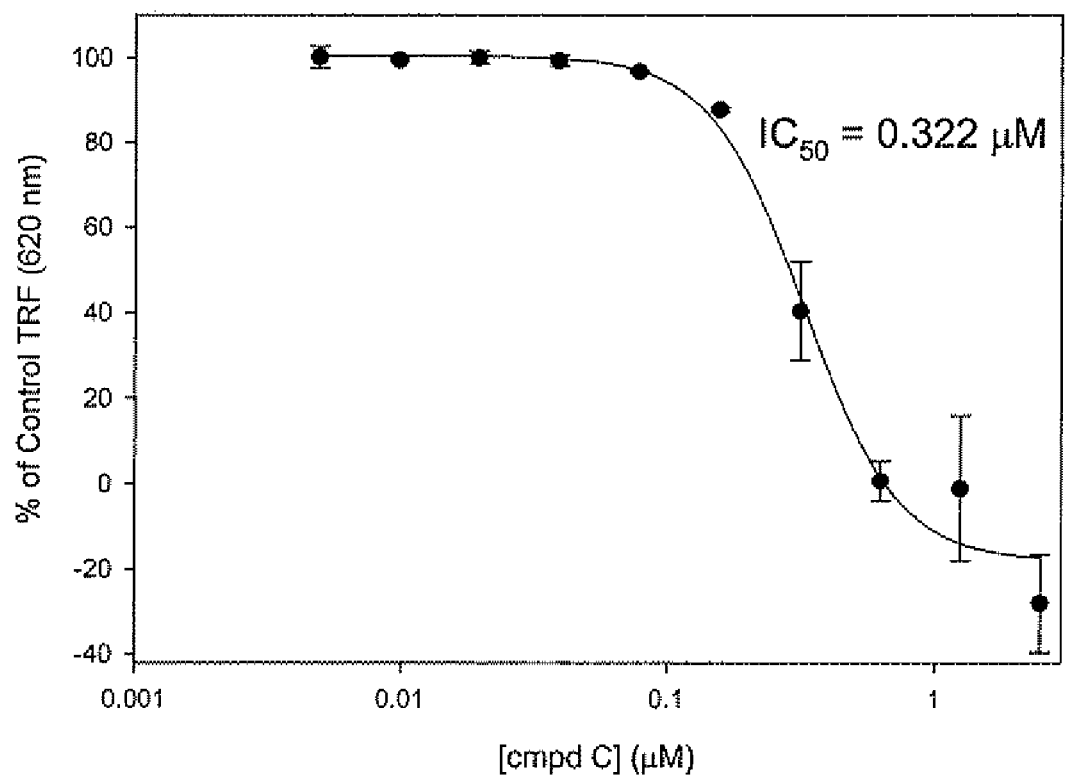
Figure 9D:
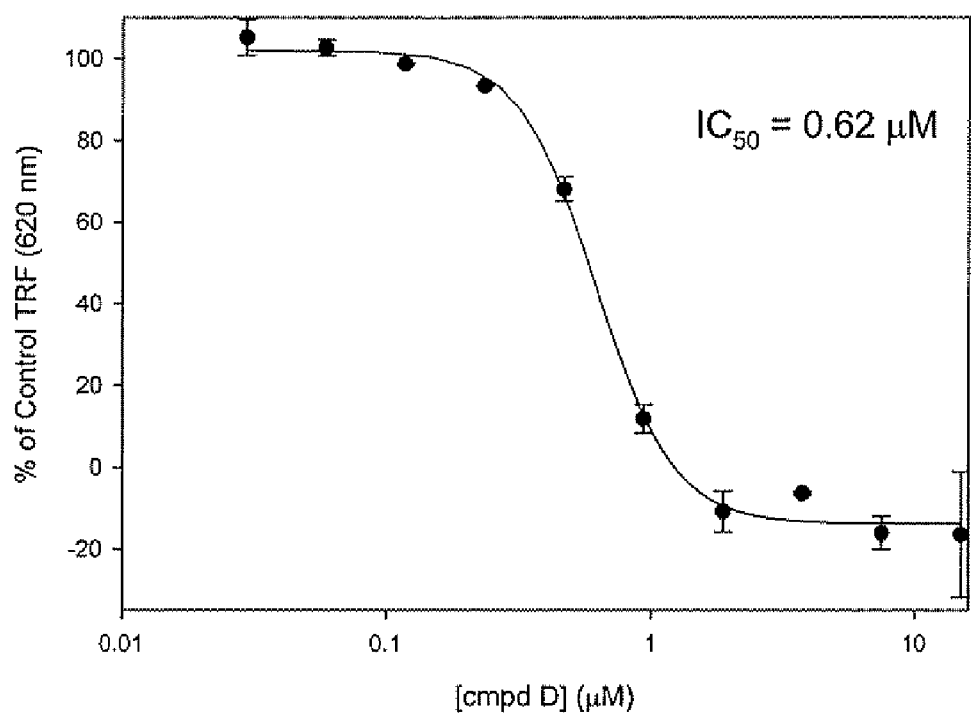

The PARP-1 derived time resolved fluorescence signal is reduced by the addition of CD38, in Step 1, due to CD38 dependent consumption of the NAD$^+$/B-NAD$^+$ mixture. Thus, time resolved fluorescence intensity is observed to be inversely proportional to CD38 catalytic activity in FIG. 8. The greater the CD38 activity in Step 1, the greater the consumption of NAD$^+$/B-NAD$^+$, and the lower the time resolved fluorescence signal at 620 nm generated in Steps 2-4 from PARP dependent consumption of residual B-NAD$^+$.

Increased CD38 activity in this competition assay leads to decreased PARP dependent time resolved fluorescence signal (hv) at 620 nm, while decreased CD38 activity in this competition assay leads to increased PARP dependent time resolved fluorescence signal (hv) at 620 nm.

Therefore, inhibition of CD38 in Step 1 manifests an increase in time resolved fluorescence signal, and the assay is ideal for identifying CD38 inhibitors in high-throughput (≧96 well format) from large compound libraries. The concentration of inhibitor required for 50% inhibition of 6 nM CD38 is determined by plotting the increase in time resolved fluorescence signal against increasing inhibitor concentration, as shown in FIGS. 9A, 9B, 9C and 9D for compounds A, B, C and D (respectively).

Inhibitors of PARP-1 may be identified by removing CD38 from Step 1 (Scheme 3), leaving a direct assay for modulators of PARP-1 activity. This direct PARP-1, assay as described above and illustrated in FIG. 7, is required for determining the selectivity of the CD38 inhibitors identified in Scheme 3. Molecules that inhibit CD38 activity, as assayed by the CD38/PARP TRF assay, but do not inhibit PARP-1 activity, are confirmed as specific inhibitors of CD38 activity. Compounds A, B, C and D, which do not inhibit PARP-1 at concentrations ≦10 μM, as shown in FIG. 10, are examples of confirmed, selective inhibitors of CD38 activity.

What is claimed is:

1. A method for determining if a test compound inhibits the production of ADP resulting from the reaction of CD38 with $NAD^+$ to produce ADPR, subsequent reaction of the ADPR with ADPRase to produce AMP and subsequent reaction of the AMP with myokinase and ATP to produce ADP, said method comprising:
   (a) forming a first reaction mixture consisting essentially of $NAD^+$, CD38, ATP, ADPRase, myokinase and the test compound in a buffer solution, and forming a second reaction mixture consisting essentially of $NAD^+$, CD38, ATP, ADPRase and myokinase in a buffer solution:
   (b) incubating both the first reaction mixture and the second reaction mixture;
   (c) adding a luciferin/luciferase reagent to generate luminescence by reacting with any residual ATP to both the first reaction mixture and the second reaction mixture;
   (d) measuring the luminescence resulting from step (c) in both the first reaction mixture and the second reaction mixture; and
   (e) comparing the luminescence generated in step (c) between the first reaction mixture and the second reaction mixture
   wherein more luminescence in the first reaction mixture as compared to the second reaction mixture indicates that the test compound inhibits production of ADP.

2. The method according to claim 1 wherein the CD38 in step (a) is a CD38 ectoenzyme consisting of residues 45-299 with either: (i) a YV amino terminal fusion and mutations N100D, N164A, N209D and N219D; or (ii) a 6 H amino terminal fusion and mutations N100D, N164A, N209D and N219D.

3. The method according to claim 1 wherein the concentration of $NAD^+$ in step (a) is between 12.5 micromolar and 25 micromolar.

4. The method according to claim 1 wherein the concentration of CD38 in step (a) is between 111 pM and 200 pM.

5. The method according to claim 1 wherein the concentration of ADPRase in step (a) is between 1.25 and 10 nM.

6. The method according to claim 1 wherein the concentration of myokinase in step (a) is between 50 nM and 100 nM.

7. The method according to claim 1 wherein the reaction in step (a) is allowed to incubate between about 20 and about 60 minutes.

8. A method for determining if a test compound is an inhibitor of CD38 activity, said method comprising:
   (a) determining if said test compound inhibits the production of ADP resulting from the reaction of CD38 with $NAD^+$ to produce ADPR, subsequent reaction of the ADPR with ADPRase to produce AMP and subsequent reaction of the AMP with myokinase and ATP to produce ADP, said method comprising:
   (i) forming a first reaction mixture consisting essentially of $NAD^+$, CD38, ATP, ADPRase, myokinase and the test compound in a buffer solution, and forming a second reaction mixture consisting essentially of $NAD^+$, CD38, ATP, ADPRase and myokinase in a buffer solution:
   (ii) incubating both the first reaction mixture and the second reaction mixture;
   (iii) adding a luciferin/luciferase reagent to generate luminescence by reacting with any residual ATP to both the first reaction mixture and the second reaction mixture;
   (iv) measuring the luminescence resulting from step (a)(iii) in both the first reaction mixture and the second reaction mixture; and
   (v) comparing the luminescence generated in step (a)(iii) between the first reaction mixture and the second reaction mixture
   wherein more luminescence in the first reaction mixture as compared to the second reaction mixture indicates that the test compound inhibits production of ADP; and
   (b) determining if said test compound is an inhibitor of ADPRase or myokinase in a method comprising the steps of:
   (i) combining ADPR with ADPRase, ATP, myokinase and the test compound in a buffer solution to form a first reaction mixture and combining ADPR with ADPRase, ATP and myokinase in a buffer solution to form a second reaction mixture;
   (ii) incubating both the first reaction mixture and the second reaction mixture;
   (iii) adding a luciferin/luciferase reagent to generate luminescence by reacting with any residual ATP to both the first reaction mixture and the second reaction mixture;
   (iv) measuring the luminescence resulting from step (b)(iii) in both the first reaction mixture and the second reaction mixture; and
   (iv) comparing the luminescence generated in step (b)(iii) between the first reaction mixture and the second reaction mixture;
   wherein more luminescence in the first reaction mixture as compared to the second reaction mixture indicates that the test compound inhibits ADPRase or myokinase
   wherein inhibition by the test compound in step (a) followed by lack of inhibition by the test compound in step (b) indicates that the test compound is an inhibitor of CD38 activity.

* * * * *